US012004957B2

(12) United States Patent  (10) Patent No.: US 12,004,957 B2
Sansone et al.  (45) Date of Patent: Jun. 11, 2024

(54) CONSTRAINED SHOULDER AND HIP ARTHROPLASTY

(71) Applicant: 4S Fx Solutions, LLC, Monona, WI (US)

(72) Inventors: Jason Sansone, Monona, WI (US); Edward Raleigh, Sun Prairie, WI (US); Robert Godfrey, Sun Prairie, WI (US)

(73) Assignee: 4S Fx Solutions, LLC, Monona, WI (US)

( * ) Notice: Subject to any disclaimer, the term of this patent is extended or adjusted under 35 U.S.C. 154(b) by 0 days.

(21) Appl. No.: 17/368,324

(22) Filed: Jul. 6, 2021

(65) Prior Publication Data

US 2022/0061996 A1  Mar. 3, 2022

Related U.S. Application Data

(60) Provisional application No. 63/048,318, filed on Jul. 6, 2020.

(51) Int. Cl.
*A61F 2/36* (2006.01)
*A61F 2/40* (2006.01)
*A61F 2/30* (2006.01)

(52) U.S. Cl.
CPC .......... *A61F 2/3609* (2013.01); *A61F 2/4014* (2013.01); *A61F 2002/30433* (2013.01); *A61F 2002/30507* (2013.01); *A61F 2002/30578* (2013.01)

(58) Field of Classification Search
CPC .................. A61F 2/3609; A61F 2/4014; A61F 2002/30433; A61F 2002/30507; A61F 2002/30578; A61F 2002/4085; A61F 2/4081
See application file for complete search history.

(56) References Cited

U.S. PATENT DOCUMENTS 3,869,730 A * 3/1975 Skobel ................ A61F 2/30742
 623/19.12
5,514,182 A * 5/1996 Shea ......................... A61F 2/32
 623/23.4
8,845,740 B2 * 9/2014 Boyden ..................... A61F 2/40
 623/20.14

(Continued)

FOREIGN PATENT DOCUMENTS

WO  WO-2018191420 A1 * 10/2018 ......... A61B 17/1778

*Primary Examiner* — Matthew J Lawson
*Assistant Examiner* — Cassidy N Stuhlsatz
(74) *Attorney, Agent, or Firm* — Casimir Jones, S.C.; Jason R. Bond

(57) ABSTRACT

The present invention provides systems, devices, and methods for using two or more flexible bands to constrain shoulder and/or hip replacement components to reduce dislocation and/or instability (e.g., constrain the glenosphere against a glenosphere recess, or constrain a femoral head against an acetabular component). In certain embodiments, one end of the flexible bands are attached to, or are held by, a first ring (e.g., expandable ring, such as a snap ring) that is configured to be operably connected (e.g., via a humeral baseplate) to a humeral stem, while another end of the flexible bands are attached to, or are held by, a second ring (e.g., flat ring, washer, annular, hoop, or orbital) that is configured to be operably connected (e.g., via a scapular baseplate) to a scapular bone.

13 Claims, 18 Drawing Sheets

(56) References Cited

U.S. PATENT DOCUMENTS

| | | | |
|---|---|---|---|
| 2002/0120339 A1* | 8/2002 | Callaway | A61F 2/4014 |
| | | | 623/23.47 |
| 2010/0049327 A1* | 2/2010 | Isch | A61F 2/34 |
| | | | 623/19.12 |
| 2010/0087927 A1 | 4/2010 | Roche et al. | |
| 2013/0131741 A1* | 5/2013 | Kourtis | A61F 2/30756 |
| | | | 606/86 R |
| 2017/0156873 A1 | 6/2017 | Hopkins | |
| 2018/0193150 A1* | 7/2018 | Winslow | A61F 2/4003 |
| 2019/0015193 A1* | 1/2019 | Kovacs | A61F 2/08 |
| 2019/0301090 A1 | 10/2019 | Jessup et al. | |
| 2019/0328536 A1* | 10/2019 | Martin | A61F 2/4014 |
| 2020/0188121 A1* | 6/2020 | Boux de Casson | |
| | | | A61F 2/30734 |
| 2020/0188123 A1* | 6/2020 | Hodorek | A61F 2/30749 |

\* cited by examiner

FIG. 5A
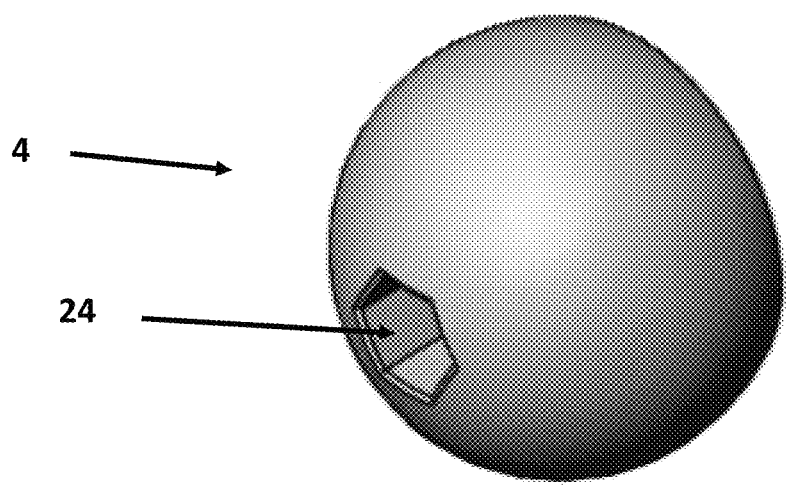
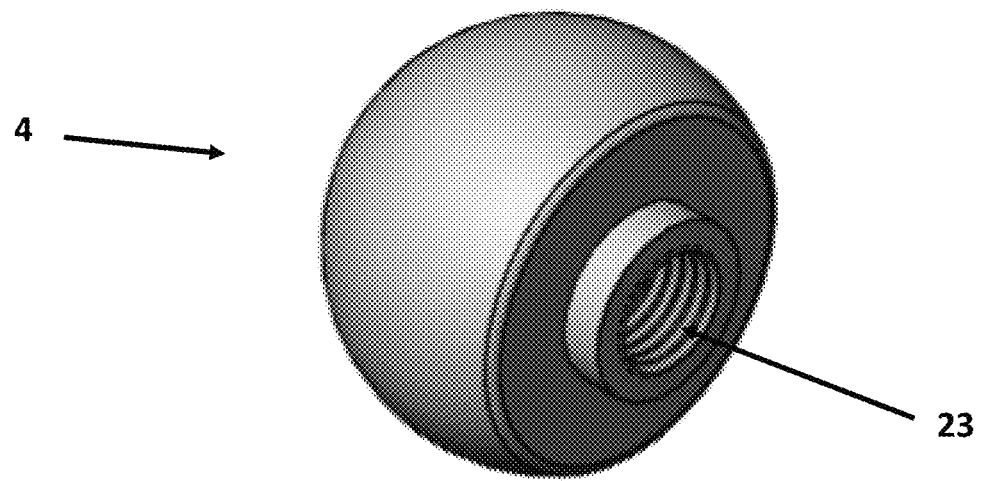
FIG. 5B

FIG. 13D SECTION A-A 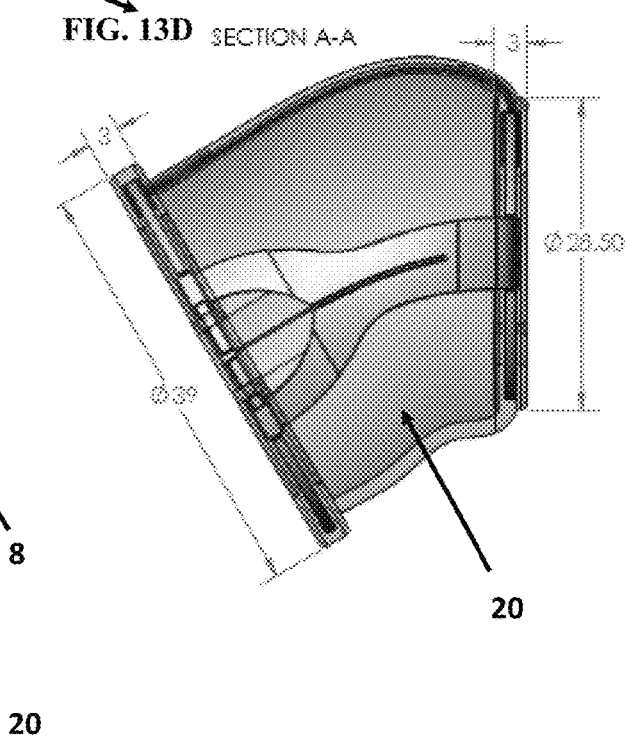

FIG. 16A
FIG. 16B
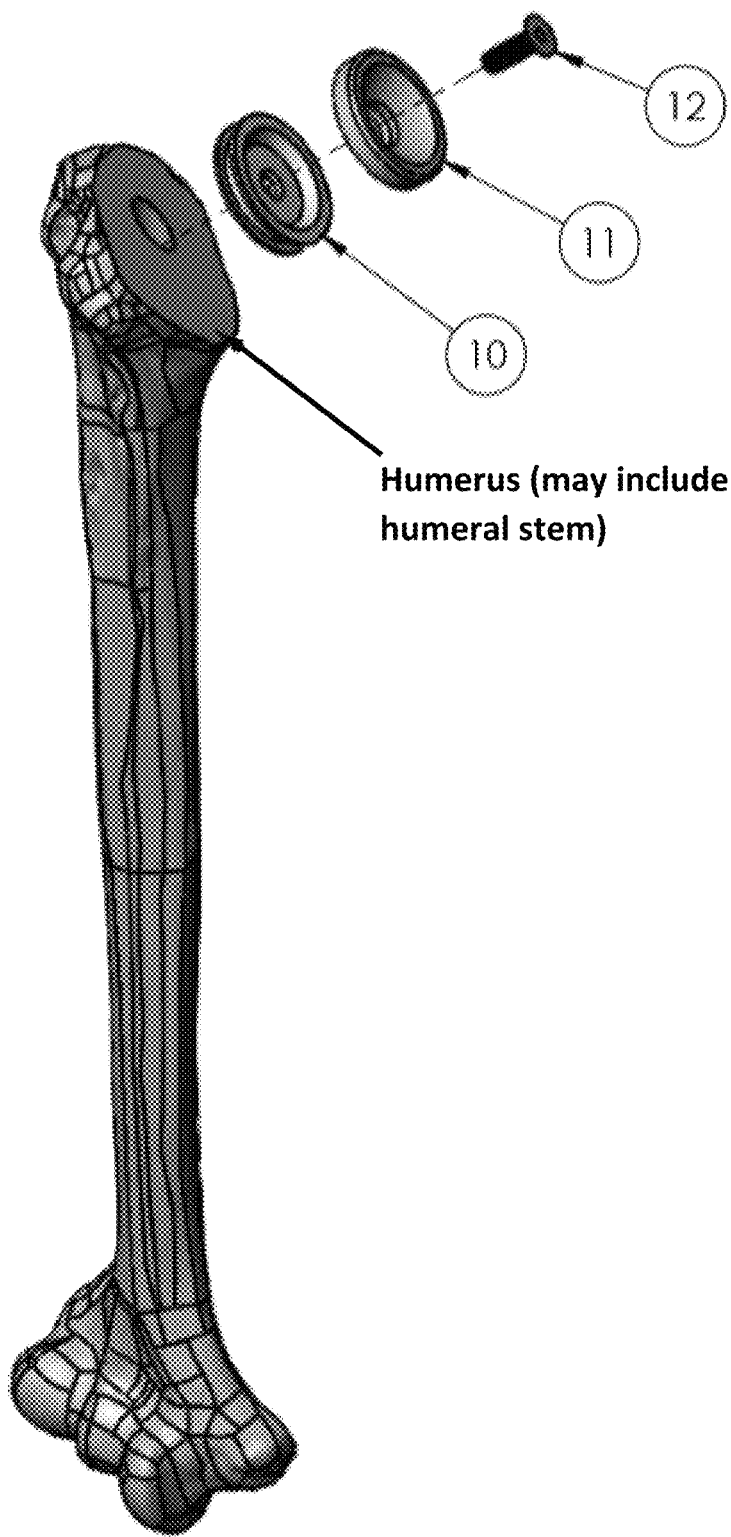
Humerus (may include humeral stem)
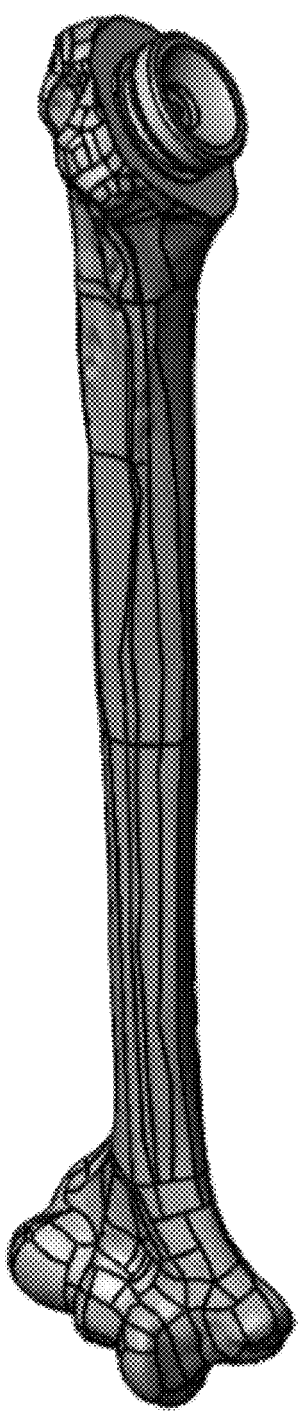

CONSTRAINED SHOULDER AND HIP ARTHROPLASTY

The present application claims priority to U.S. Provisional application Ser. No. 63/048,318 filed Jul. 6, 2000, which is herein incorporated by reference in its entirety.

FIELD OF THE INVENTION

The present invention provides systems, devices, and methods for using two or more flexible bands to constrain shoulder and/or hip replacement components to reduce dislocation and/or instability (e.g., constrain the glenosphere against a glenosphere recess, or constrain a femoral head against an acetabular component). In certain embodiments, one end of the flexible bands are attached to, or are held by, a first ring (e.g., expandable ring, such as a snap ring) that is configured to be operably connected (e.g., via a humeral baseplate) to a humeral stem, while another end of the flexible bands are attached to, or are held by, a second ring (e.g., flat ring, washer, etc.) that is configured to be operably connected (e.g., via a scapular baseplate) to a scapular bone. In some embodiments, an outer sleeve (e.g., cylindrical silicone sleeve) is employed that is sized to generally enclose the flexible bands, the glenosphere, and glenosphere recess, or conversely, for the hip joint, the femoral head and acetabular component liner.

BACKGROUND

Proximal humerus fractures are common. Often, they heal without operative intervention. However in a minority of cases, surgical management is required. Typically, this involves open reduction internal fixation. However, occasionally the trauma to the humeral head is not re-constructible and the patient is better served with immediate arthroplasty. The arthroplasty of choice in most traumatic indications is reverse total shoulder arthroplasty.

However, reverse total shoulder arthroplasty in the setting of proximal humerus fracture is often complicated by instability/dislocation of the arthroplasty components. This is due to multiple factors, including destabilizing fracture lines, pliable soft tissues, and injury-related nerve palsies. In order to mitigate the risk of instability/dislocation, surgeons must often lengthen and/or lateralize the humerus relative to the glenoid. While this is an effective means by which to decrease the risk of dislocation, altering the glenohumeral relationship can lead to tuberosity nonunion, deltoid failure, acromial stress fracture, and/or axillary neuropraxia. Given this, the need for an intrinsically stable reverse total shoulder arthroplasty is clear.

SUMMARY OF THE INVENTION

The present invention provides systems, devices, and methods for using two or more flexible bands to constrain shoulder and/or hip replacement components to reduce dislocation and/or instability (e.g., constrain the glenosphere against a glenosphere recess, or constrain a femoral head against an acetabular component). In certain embodiments, one end of the flexible bands are attached to, or are held by, a first ring (e.g., expandable ring, such as a snap ring) that is configured to be operably connected (e.g., via a humeral baseplate) to a humeral stem, while another end of the flexible bands are attached to, or are held by, a second ring (e.g., flat ring, washer, etc.) that is configured to be operably connected (e.g., via a scapular baseplate) to a scapular bone. In some embodiments, an outer sleeve (e.g., cylindrical silicone sleeve) is employed that is sized to generally enclose the flexible bands, the glenosphere, and glenosphere recess, or conversely, for the hip joint, the femoral head and acetabular component liner.

In some embodiments, provided herein are systems (and kits and devices) comprising: a retainer assembly comprising: a) a first ring (e.g., expandable ring, such as a snap ring or other retaining ring) that attaches to a humeral baseplate and/or humeral stem, b) a second ring (e.g., washer, flat ring, orbital ring, etc.) that attaches to a scapular baseplate and/or scapular bone, c) a first flexible band: A) attached to, or configured to be attached to or held by, the first ring, and B) attached to, or configured to be attached to or held by, the second ring, d) a second flexible band: A) attached to, or configured to be attached to or held by, the first ring, and B) attached to, or configured to be attached to or held by, the second ring, and e) a retainer assembly outer sleeve that: i) extends from the first ring to the second ring, and ii) is sized to generally enclose the first and second flexible bands and a glenosphere or femoral head used in shoulder or hip arthroplasty, respectively, wherein the retainer assembly aids in constraining the system from dislocation and/or instability when the system is installed in a subject's shoulder joint or hip joint. In particular embodiments, the retainer assembly aids in constraining said glenosphere from dislocating from a glenosphere recess when the system is installed in the subject's shoulder joint.

In some embodiments, provided herein are systems (and kits and devices) comprising: a) a scapular baseplate comprising: i) a scapular bone connecting component, ii) a glenosphere connecting component; and iii) a second ring connecting component; b) a humeral baseplate comprising: i) a humeral bone, and/or humeral stem, connecting component, ii) a glenosphere recess, and iii) a first ring connecting component, c) a glenosphere comprising: i) a top surface that articulates with the glenosphere recess, and ii) a bottom surface that attaches to the glenosphere connecting component of the scapular baseplate; d) a retainer assembly comprising: i) a first ring (e.g., expandable ring, such as a snap ring or other retaining ring) that attaches to the first ring connecting component of the humeral baseplate, ii) a second ring comprising a scapular baseplate connecting component, iii) a first flexible band: A) attached to, or configured to be attached to or held by, the first ring, and B) attached to, or configured to be attached to or held by, the second ring, iv) a second flexible band: A) attached to, or configured to be attached to or held by, the first ring, and B) attached to, or configured to be attached to or held by, the second ring, wherein the retainer assembly aids in constraining the system from dislocation and/or instability when the system is installed in a subject's shoulder joint.

In certain embodiments, the first ring further comprises: A) a first flexible band attachment or holder site, and B) a second flexible band attachment or holder site. In particular embodiments, the first and second flexible band attachment or holder sites are notches or protrusions in the first ring. In other embodiments, the second ring further comprises: A) first flexible band holder or attachment sites, and B) second flexible band holder or attachment sites. In other embodiments, the first and second flexible band holder or attachment sites are notches or protrusions.

In certain embodiments, the first ring is expandable (e.g., and the second ring is expandable or non-expandable). In other embodiments, the second ring is expandable (e.g., and the first ring is expandable or non-expandable).

In additional embodiments, the retainer assembly further comprises: v) a third flexible band: A) attached to, or configured to be attached to or held by, the first ring, and B) attached to, or configured to be attached to or held by, the second ring. In some embodiments, the first ring further comprises: A) a first flexible band attachment or holder site, B) a second flexible band attachment or holder site, and C) a third flexible band attachment or holder site. In particular embodiments, the first ring further comprises: A) first flexible band holder or attachment site, B) second flexible band holder or attachment site, and C) third flexible band holder or attachment site. In some embodiments, the first flexible band would be in an anterior position when the system is installed in the subject's shoulder area, the second flexible band would in a posterior position when installed in the subject's shoulder area, and the third flexible band would be in a superior position when installed in the subject's shoulder area.

In some embodiments, the retainer assembly further comprises a retainer assembly outer sleeve that extends from the first ring to the second ring covering one or both sides of the first and second flexible bands. In particular embodiments, the retainer assembly outer sleeve surrounds the glenosphere and glenosphere recess when installed in the subject's shoulder area. In further embodiments, the retainer assembly outer sleeve comprises a biocompatible flexible material. In further embodiments, the biocompatible flexible material comprises silicone or similar material. In some embodiments, the retainer assembly outer sleeve comprises: i) a generally cylindrical outer wall, ii) a lateral split in the cylindrical wall (e.g., to allow the sleeve to be expanded thereby allowing the glenosphere recess to be installed during surgery), and iii) an aperture for the scapular bone connecting component (e.g., scapular baseplate dowel pin).

In particular embodiments, the scapular base plate comprises titanium or similar metal. In further embodiments, the scapular bone connecting component comprises at least two or three apertures each sized for a bone screw. In further embodiments, the systems and kits further comprise two or three of the bone screws. In some embodiments, the scapular baseplate has a diameter between 25 and 31 mm (e.g., 25, 26, 27, 28, 29, 30, or 31 mm). In particular embodiments, the scapular baseplate further comprises: iii) a connecting component (e.g., dowel pin) configured to connect to the scapular baseplate connecting component (e.g., dowel pin hole or aperture) of the second ring. In further embodiments, the connecting component (e.g., dowel), when connected to the scapular baseplate connecting component, prevents the second ring from rotating when the system is installed in the subject's shoulder area and the shoulder area is rotated. In some embodiments, the connecting component comprises a dowel pin or rod.

In further embodiments, the glenosphere connecting component comprises a threaded post. In certain embodiments, the threaded post has a diameter of about 5-7 mm.

In particular embodiments, the humeral baseplate is a single unitary piece. In other embodiments, the humeral baseplate comprises: i) a humeral adapter tray (e.g., that comprises the first ring connecting component), and ii) a humeral liner that comprises the glenosphere recess. In certain embodiments, the humeral adapter tray comprises CoCr alloy or other metal. In particular embodiments, the first ring connecting component of the humeral adapter tray has a diameter of about 26-29 mm. In some embodiments, the humeral liner comprises a polymer. In further embodiments, the polymer comprises ultra-high molecular weight polyethylene.

In certain embodiments, the glenosphere recess of the humeral liner has a diameter of 18-22 mm (e.g., 18, 19, 20, 21, or 22 mm). In particular embodiments, the humeral adapter tray comprises a first aperture for a screw, and the humeral liner comprises a second aperture for the screw. In some embodiments, the systems further comprise the screw.

In some embodiments, the first ring connecting component comprises a peripheral recess in the humeral assembly (e.g., humeral adapter tray). In further embodiments, the peripheral first ring recess is circular or generally circular. In other embodiments, the humeral baseplate is circular or generally circular.

In other embodiments, the glenosphere comprises wrought CoCr alloy or other metal. In certain embodiments, the top surface of the glenosphere comprises an aperture sized for a tool to turn the glenosphere to tighten onto the glenosphere connecting component (e.g., threaded post). In some embodiments, the bottom surface of the glenosphere comprises a threaded aperture. In other embodiments, the glenosphere has a height of about 25-30 mm (e.g., 25, 26, 27, 28, 29, or 30 mm), and a width at the widest point of about 30-34 mm (e.g., 30, 31, 32, 33, or 34 mm).

In particular embodiments, the first ring has a circular or generally circular shape. In further embodiments, the first ring has the general shape of a flat ring. In some embodiments, the first ring is expandable by force, and will return to original size when force is removed. In further embodiments, the first ring comprises a snap ring shape having first and second openings for the ends of snap ring pliers that can be used to expand the snap ring by force. In other embodiments, the first and second openings can be tied together in a non-expandable configuration by suture thread. In particular embodiments, the first ring comprises memory shape material (e.g., metal, nitinol). In further embodiments, the first ring comprises generally a ring shape (e.g., circular, offset circle, oval, etc.) and has a diameter of 28-32 mm and a thickness of about 1-2 mm.

In some embodiments, the second ring has a general shape of a flat ring. In certain embodiments, the second ring has a general ring (e.g., circular, offset circle, oval, etc.) shape and has a diameter of about 24-29 mm (e.g., 24, 25, 26, 27, 28, or 29 mm) and a thickness of about 1-2 mm. In further embodiments, the second ring comprises metal. In further embodiments, the metal comprises stainless steel, CoCr alloy, or similar metal.

In other embodiments, the first and/or second (and/or third) flexible band is about 56-70 mm in length (e.g., 56 . . . 60 . . . 65 . . . 70 mm). In some embodiments, the first and/or second (and/or third) flexible band is about 2-20 mm (e.g., 3, 4, 5, 6, 7, 8, or 9 mm) in width. In additional embodiments, the first and/or second (and/or third) flexible band is about 0.2-1.0 mm in thickness.

In some embodiments, at least one of the flexible bands has a general Y-shape (e.g., so one end is split to span where a snap ring comes together). In other embodiments, the first flexible band: i) has a first end that attaches to, or is held by, the second ring, and ii) has second and third ends that attach to, or are held by, the first ring. In further embodiments, the first, second, and/or third ends comprise loops. In other embodiments, the second (and or third) flexible band: i) has a first end that attaches to, or is held by, the second ring, and ii) has a second end that attaches to, or is held by, the first ring. In some embodiments, the first and/or second ends comprise loops (e.g., folded back to form loops, then glued or heated). In other embodiments, the first and/or second flexible band: i) has first and second ends attached to the first ring, and ii) a general mid-point that is looped through and held by the second ring. In further embodiments, the first and/or second (and or third) flexible band: i) has first and second ends attached to the second ring, and ii) a general mid-point that is looped through and held by the first ring. In other embodiments, the first and/or second bands comprise a polymer and/or fabric.

In some embodiments, the first and/or second bands are composed of a braided, woven, or knitted material. In additional embodiments, the first and/or second bands comprise a material selected from the group consisting of: polyethylene, polypropylene, and a polyester. In certain embodiments, the first and/or second (or third) flexible bands allow between 5 and 20 percent elongation under applied load (e.g., 5 . . . 7 . . . 11 . . . 14 . . . 17 . . . 20 percent). In other embodiments, the first and/or second flexible bands allow between 13 and 15 percent elongation under applied load.

In particular embodiments, the systems further comprise a third (and fourth) flexible band: A) attached to, or configured to be attached to or held by, the second ring, and B) attached to, or configured to be attached to or held by, the first ring. In certain embodiments, the first and second flexible bands allow between 10 and 15 percent (e.g., 10, 11, 12, 14, 14, or 15 percent) elongation under applied load, and the third flexible band allows between 3 and 5 percent (e.g., 3, 4, or 5 percent) elongation under applied load.

DESCRIPTION OF THE FIGURES

FIGS. 5A and 5B depict an exemplary glenosphere. FIG. 5A depicts the top of an exemplary glenosphere (4), while FIG. 5B depicts the bottom.

FIGS. 8A and 8B depict an exemplary flexible band (7), shown as an anterior Y-shaped band. FIG. 8C shows how the flexible band could be folded to create loops.

FIG. 10A depicts an exemplary flexible band (9), shown as a superior band. FIG. 10B shows how the flexible band could be folded at the ends to create loops.

FIGS. 13A-D shows various views of an exemplary retainer assembly (14) employing three flexible straps.

FIG. 16A shows the assembly of the exemplary adapter tray (10) and exemplary humeral liner (11) onto a humeral stem using a screw (12).

FIG. 16B shows the components assembled on the humerus bone.

FIG. 18A shows a first view of a retainer assembly (14) employing two flexible straps (7 and 9). FIG. 18B is a second view of a retainer assembly (14) employing two flexible straps (7 and 9).

DETAILED DESCRIPTION

The present invention provides systems, devices, and methods for using two or more flexible bands to constrain shoulder and/or hip replacement components to reduce dislocation and/or instability (e.g., constrain the glenosphere against a glenosphere recess, or constrain a femoral head against an acetabular component). In certain embodiments, one end of the flexible bands are attached to, or are held by, a first ring (e.g., expandable ring, such as a snap ring) that is configured to be operably connected (e.g., via a humeral baseplate) to a humeral stem, while another end of the flexible bands are attached to, or are held by, a second ring (e.g., flat ring, washer, annular, hoop, or orbital) that is configured to be operably connected (e.g., via a scapular baseplate) to a scapular bone. In some embodiments, an outer sleeve (e.g., cylindrical silicone sleeve) is employed that is sized to generally enclose the flexible bands, the glenosphere, and glenosphere recess, or conversely, for the hip joint, the femoral head and acetabular component liner.

Figure 1:
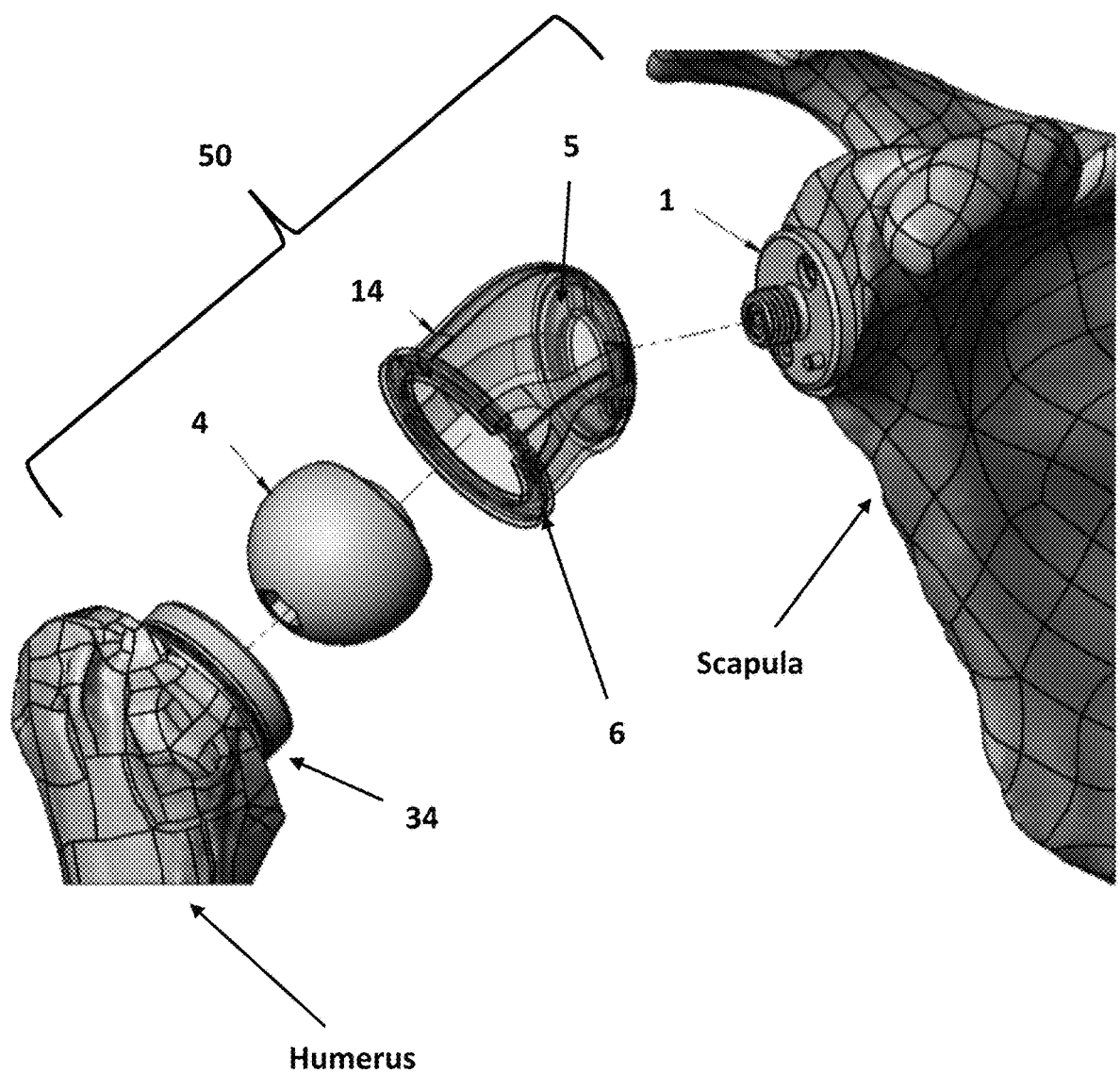
FIG. 1 shows an exemplary embodiment of the shoulder joint replacement system (50) herein and how the components are connected in a subject's shoulder. The right shoulder is shown.

FIG. 1 shows an exemplary embodiment of the shoulder joint replacement system (50) herein and how the components are connected in a subject's shoulder. The scapular baseplate (1) is implanted with screws, followed by the retainer assembly (14). The glenosphere (4) is then threaded onto the scapular baseplate, thereby securing the retainer assembly on the scapular side. The humeral baseplate (34) (e.g., constructed with parts 10-12) is mated with the glenosphere after opening the first ring of the retainer assembly (6), for example with snap ring pliers. The right shoulder is shown.

Figure 2A:
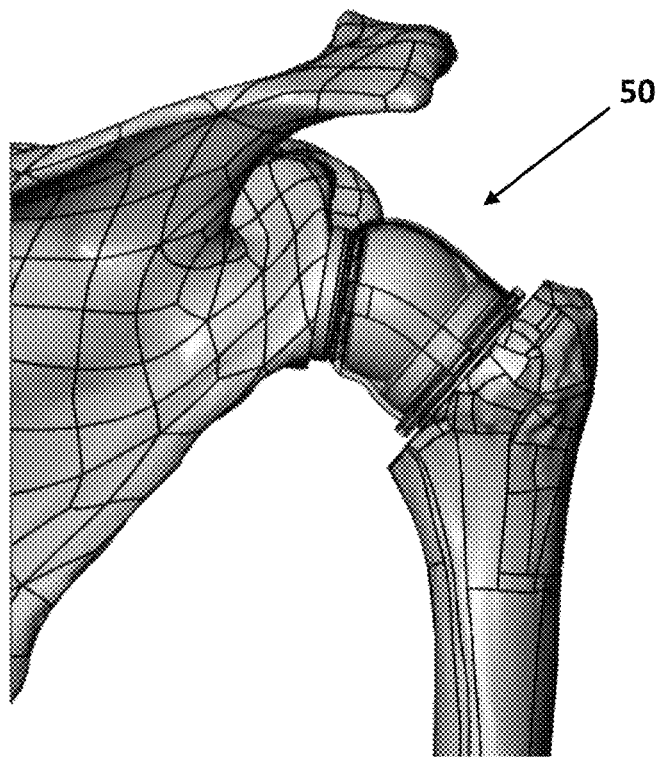
FIGS. 2A and 2B depict back and front views of an exemplary embodiment of a fully assembled shoulder joint replacement system (50). The right shoulder is shown.
Figure 2B:
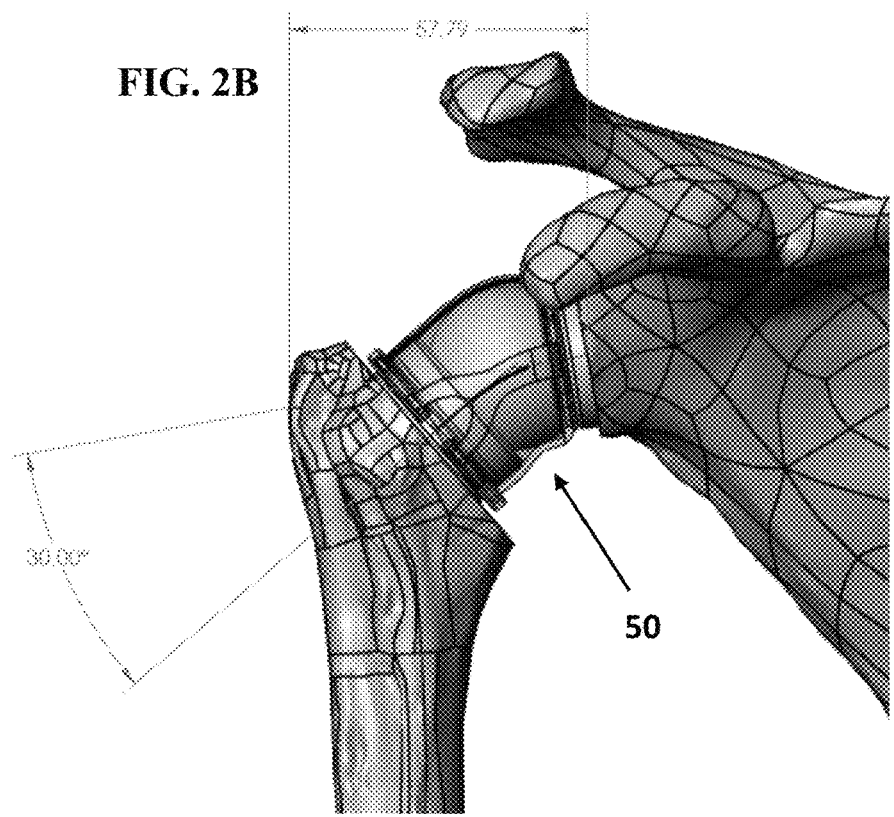

FIGS. 2A and 2B depict back and front views of an exemplary embodiment of a fully assembled shoulder joint replacement system (50). The right shoulder is shown.

Figure 3A:
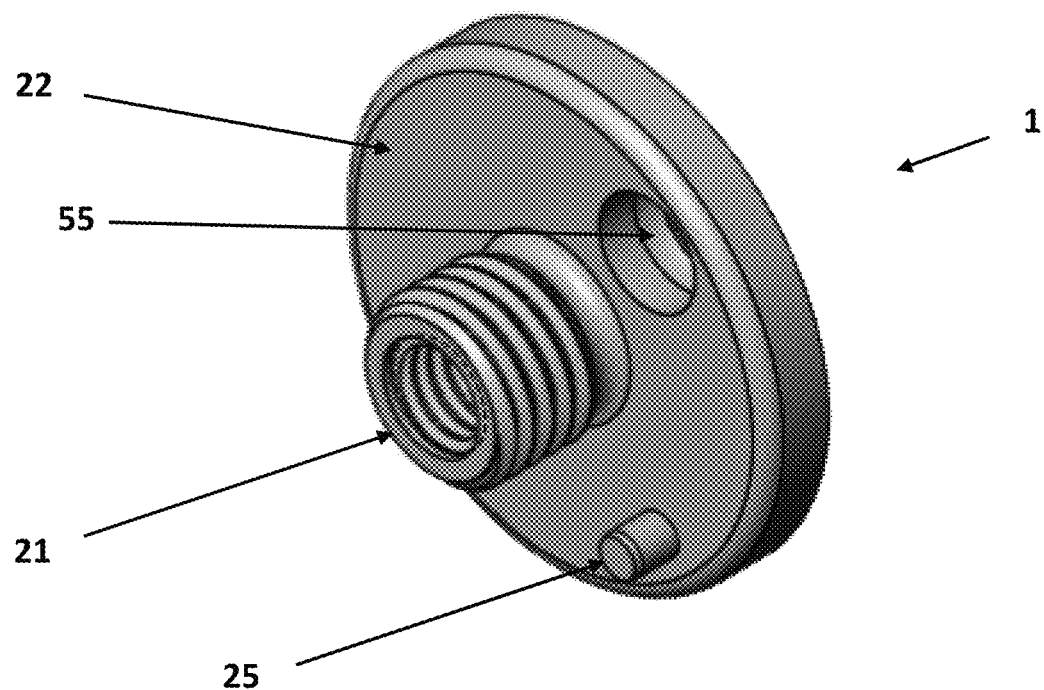
FIG. 3A depicts the front of an exemplary scapular baseplate (1).
Figure 3B:
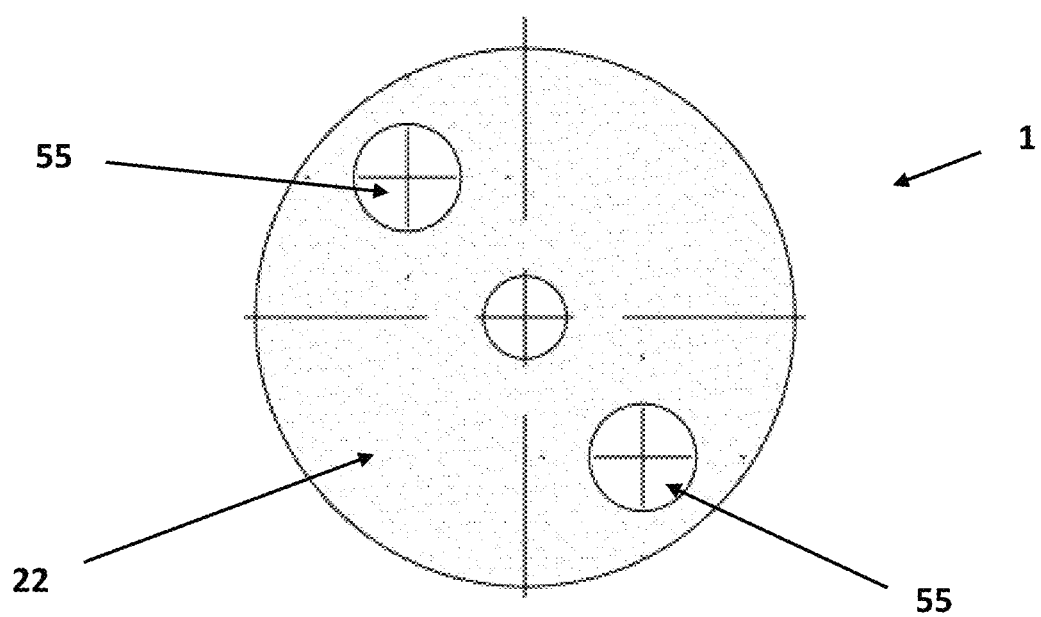
FIG. 3B shows the bottom of the exemplary scapular baseplate (1).

FIG. 3A depicts the front of an exemplary scapular baseplate (1) (e.g., 28 mm in diameter), which may be composed of a suitable Ti alloy. FIG. 3B shows the bottom of the exemplary scapular baseplate (1), which may be constructed of porous Ti (22), which stimulates bone in-growth. In general, the remaining surfaces are smooth. FIG. 3A shows a glenosphere base connecting component (21), which may be an 8 mm male threaded post situated in the center of the baseplate. The threaded post mates with the glenosphere (4), via attachment bottom hole (23), which may be corresponding female threads (see FIG. 5). The inner surface of the post (21) is threaded, and accepts a, locking compression, central screw (2) with a 6.25 mm threaded head and 4 mm outer diameter shaft. There are two 6.3 mm diameter holes (55) in the baseplate, arranged 180 degrees relative to one another, which accept side screws (3), such as 5 mm non-locking screw for fixation into the glenoid. A baseplate mating component (25) (e.g., 2.5 mm dowel pin) mates with the first ring (5), providing stability such that (5) cannot rotate relative to part 1.

Figure 4:
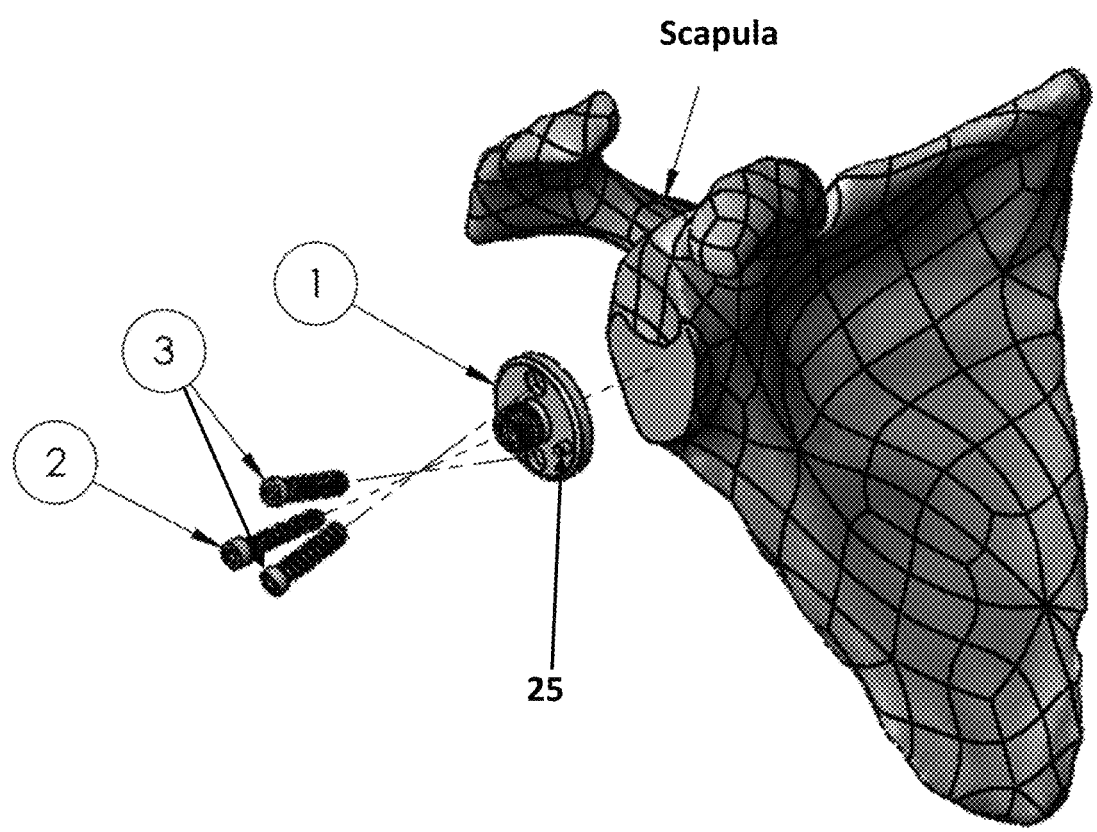
FIG. 4 depicts the assembly of an exemplary scapular baseplate (1), central screw (2), and side screws (3) onto the native scapula.

FIG. 4 depicts the assembly of an exemplary scapular baseplate (1), central screw (2), and side screws (3) onto the native scapula. The right scapula is shown for illustrative purposes, and the articular cartilage has been reamed to bleeding subchondral bone to allow for bone ingrowth. Non-locking, side screws (3) are placed through the scapular baseplate (1) followed by a locking compression, central screw (2). The baseplate (1) has a dowel pin (25) which is oriented toward the anterior portion of the scapula.

FIG. 5A depicts the top of an exemplary glenosphere (4), while FIG. 5B depicts the bottom, which includes an attachment bottom hole (23) that mates with the glenosphere connecting component (e.g., male threaded post (21)) of the scapular baseplate (1). The glenosphere has a hole on top (adjustment hole 24) where a tool can be inserted, such as a hex or Torx tool, to turn the glenosphere such that the attachment bottom hole (23) is tightened down onto the threaded post (21) of the scapular baseplate (1).

Figure 6:
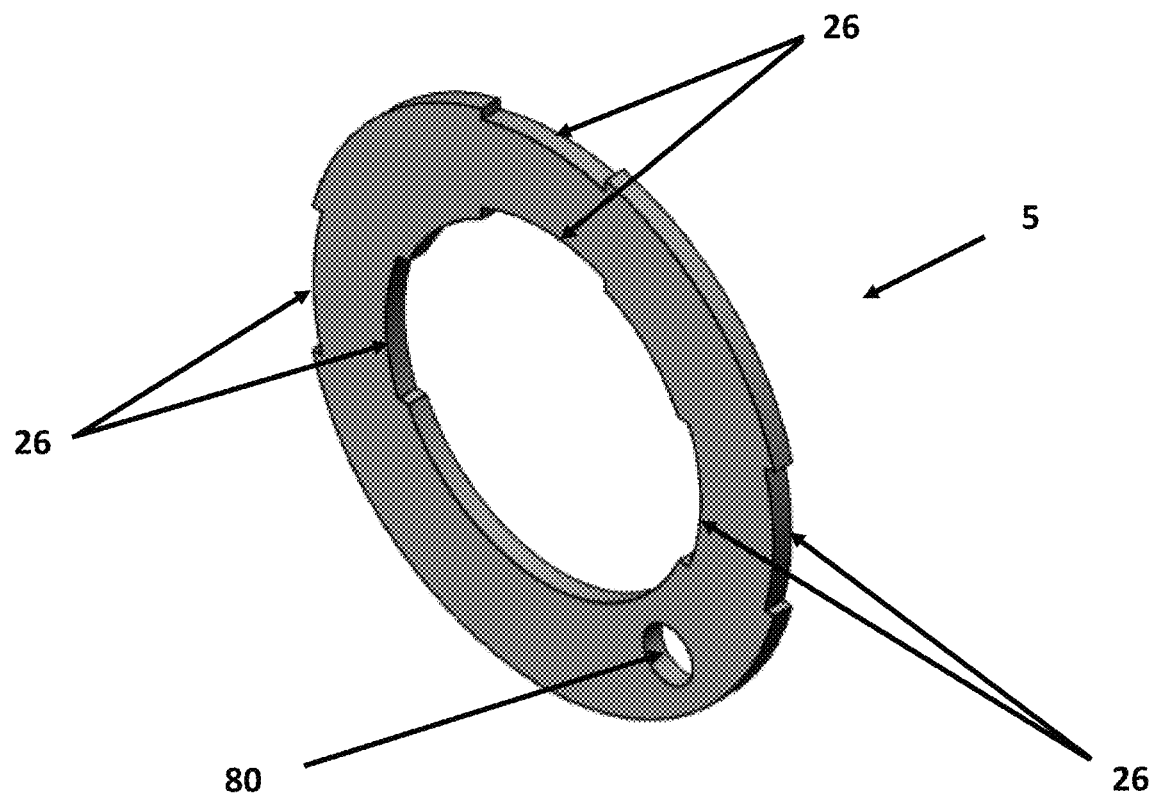
FIG. 6 depicts an exemplary second ring (5) (e.g., as a washer), with a hole (80).

FIG. 6 depicts an exemplary second ring (5), which may be a washer as shown in this figure. The second ring may be constructed from 316L stainless steel, CoCr alloy, or other suitable material. Exemplary second ring (5) contains a 2.75 mm hole (80) that accepts the 2.5 mm dowel pin located on the scapular baseplate (1), which imparts rotational control of part 5 relative to part 1. In addition, three slots are located on the second ring (5) at the anterior, superior, and posterior positions as viewed on face. These accept the flexible bands (parts 7, 8, and 9). These slots secure the location of parts 7-9 in relation to part 5.

Figure 7:
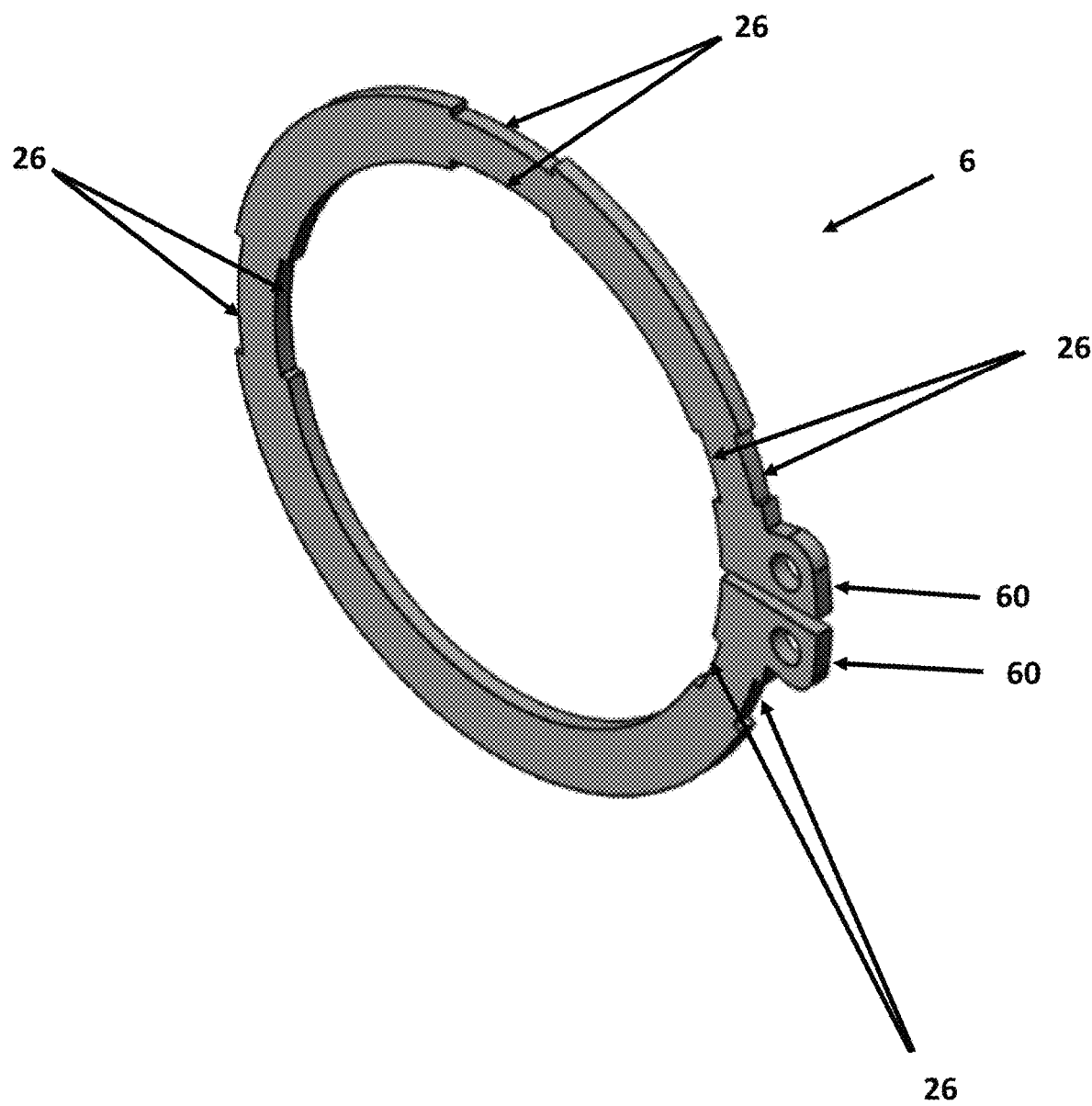
FIG. 7 depicts an exemplary first ring (6) (e.g., as a snap ring).

FIG. 7 depicts an exemplary first ring (6). The exemplary first ring is shown as a snap ring composed of nitinol. Four slots (26) are located at the anterior (7), superior (9), and posterior (8) positions as viewed on face. These accept the flexible bands. These slots secure the location of parts 7-9 in relation to part 6. In addition, the exemplary first ring (6) contains two holes which accept a snap ring pliers, allowing the surgeon to expand or open the first ring in order to deliver the humeral assembly into the retainer assembly to articulate with the scapular assembly (glenosphere) in vivo. Once the snap ring pliers are removed, the nitinol will bend back to the original circular shape. Suture will then be placed by the surgeon around the anterior flexible band and the surgeon would, in certain embodiments, thread this suture through the holes (60). Notably, this would not be necessary to the survivorship of the implant given the intrinsic material properties of the nitinol.

Figure 8A:
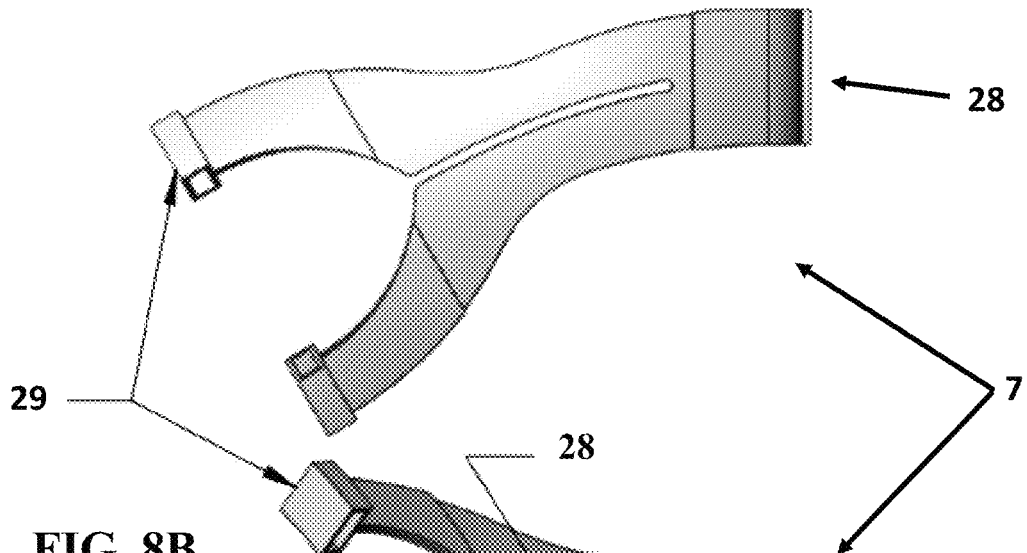
FIGS. 8A-8C show an exemplary flexible band.
Figure 8B:
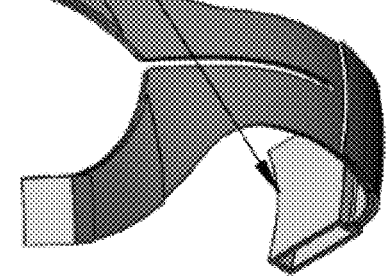
Figure 8C:
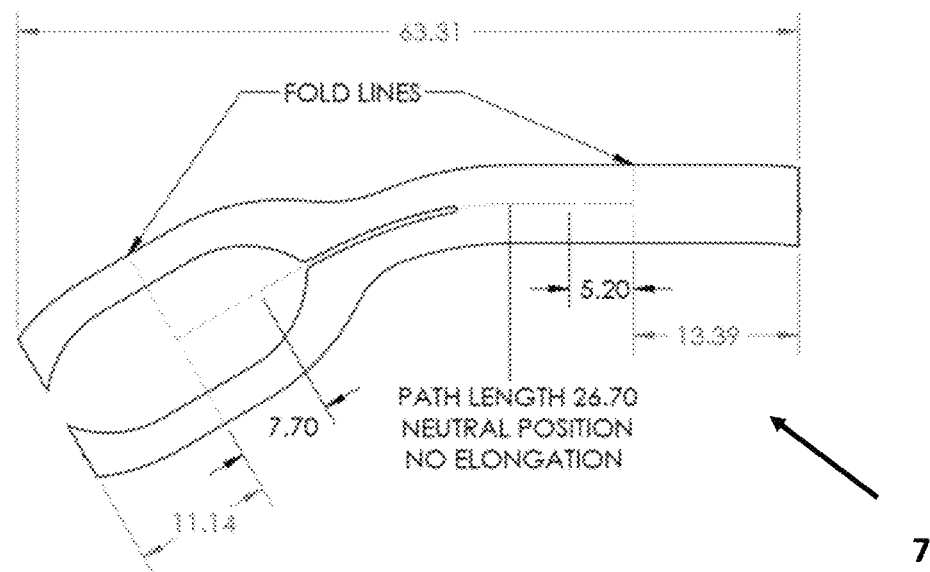

FIGS. 8A and 8B depict an exemplary flexible band (e.g., fabric band) (7), shown as an anterior Y-shaped band. FIG. 8C shows how the flexible band can be folded on itself at the ends to create loops. In certain embodiments, these bands are made of ultra-high molecular weight polyethylene (UHMWPE) (or similar material) fashioned into a tubular braid, which provides high tensile strength (e.g., load to failure: 75 kg) while allowing 15% elongation under applied load. The bands converge on one side, near part 5. They are attached to parts 5 and 6 (in corresponding slots) by doubling over on the fold lines (8C) and forming a loop (e.g., which are fixed with adhesive, ultrasonic welding, or heat staking), to which an adhesive is applied. The band is thermally annealed to the necessary length. The open portion of the Y-shape allows the humeral assembly to be delivered into the first ring (and thereby, the retainer assembly), for example, once a snap ring pliers opens the nitinol snap ring.

In certain embodiments, the flexible bands described herein are composed of materials described in US20190301090 (herein incorporated by reference), ultra-high molecular weight polyethylene, or artificial tendon material from LARS, ATEX Technologies, or SURGICALMESH. In certain embodiments, the flexible bands are braided (e.g., tubular braid), woven, or knitted structure of the material. In some embodiments, the material is polyethylene, polypropylene or polyester (or similar fabric). As long as whatever is used is formed into a braid, knit, or weave. In particular embodiments, the flexible band material is capable of being thermally annealed (shrunk to a specific length yet retain its mechanical characteristics).

Figure 9A:
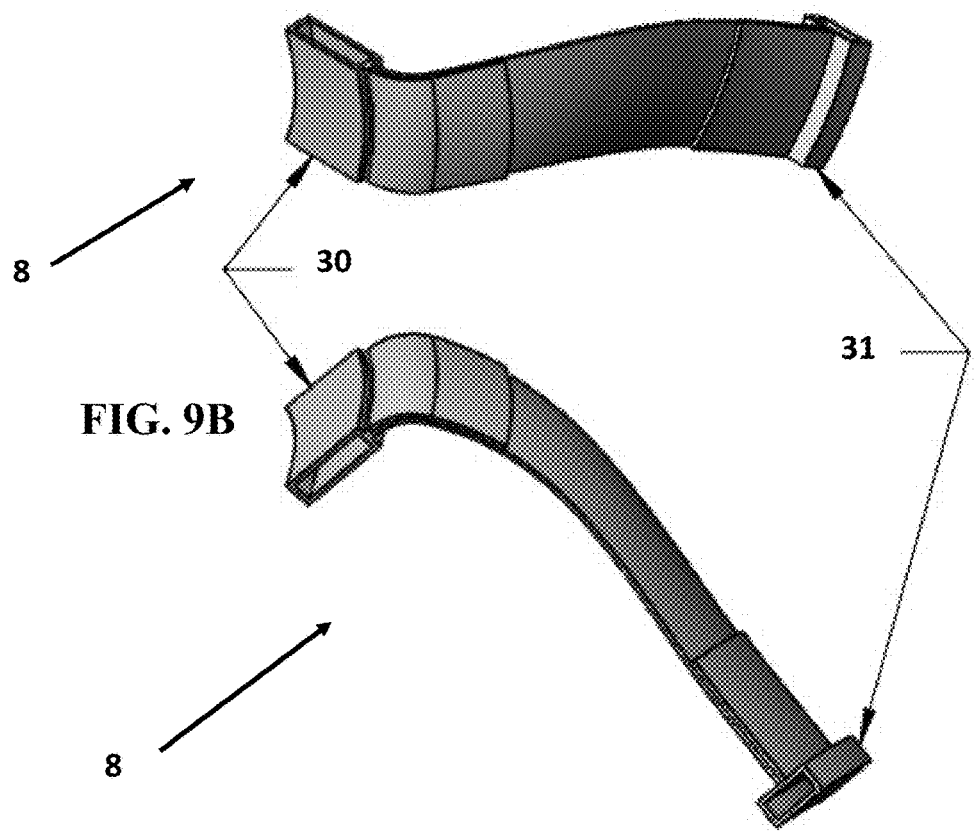
FIGS. 9A and 9B shows an exemplary flexible band (8), shown as a posterior band.
Figure 9B:
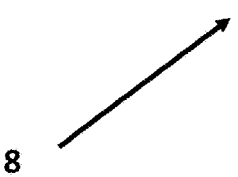
Figure 9C:
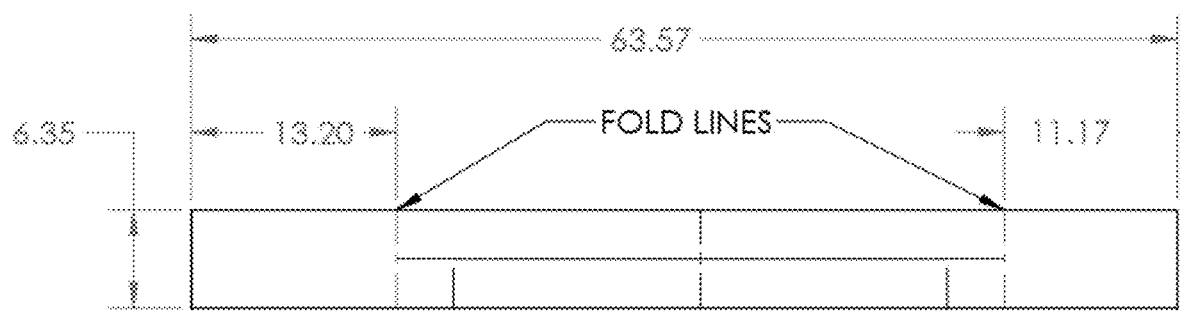
FIG. 9C shows how the flexible band could be folded at the ends to create loops (e.g., which are fixed with adhesive, ultrasonic welding, or heat staking).
Figure 9C:

FIGS. 9A and 9B show an exemplary flexible band (8), shown as a posterior band. FIG. 9C shows how the flexible band could be folded on itself at the ends to create loops. The flexible band (8) is attached to parts 5 and 6 (e.g., in corresponding slots) by doubling over on the fold lines (FIG. 9C) and forming a loop (e.g., which is fixed with adhesive, ultrasonic welding, or heat staking). The band is thermally annealed to the necessary length.

Figure 10A:
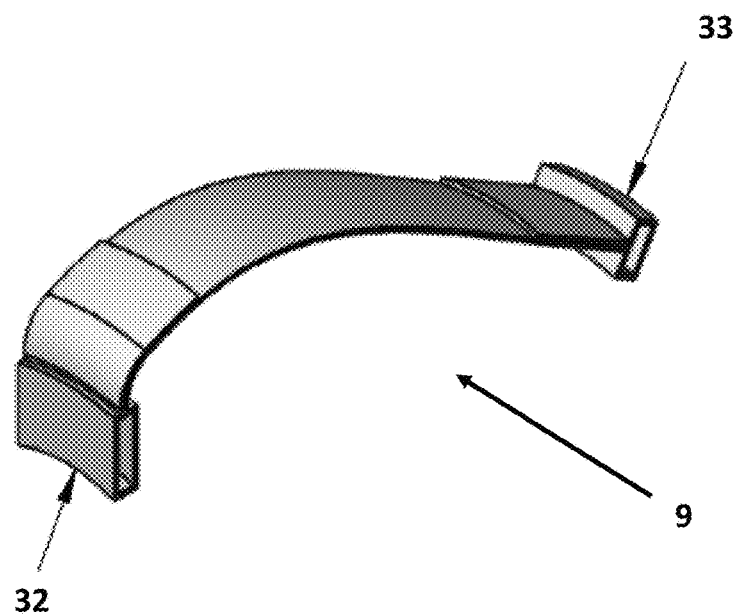
FIGS. 10A and 10B show a superior band.
Figure 10B:
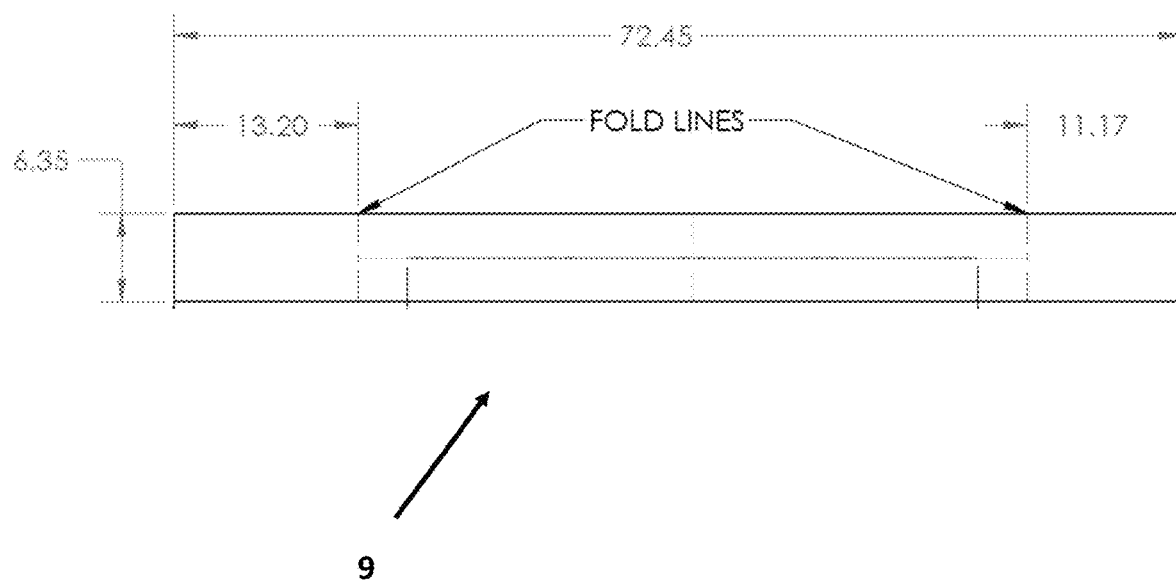

FIG. 10 depicts an exemplary flexible band (9), shown as a superior band. FIG. 10B shows how the flexible band could be folded on itself at the ends to create loops. In certain embodiments, the superior band would require about 5% elongation.

Figure 11:
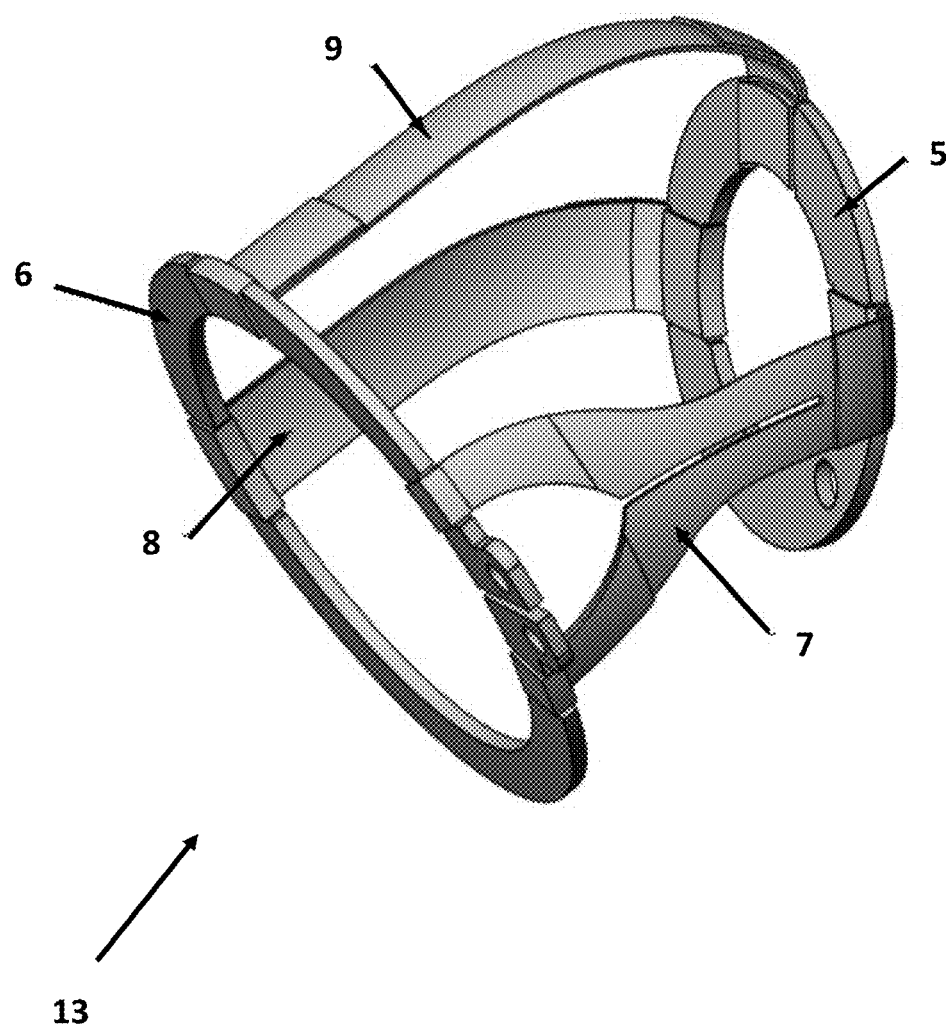
FIG. 11 shows an exemplary band assembly (13).

FIG. 11 shows an exemplary band assembly (13). This assembly includes three flexible bands (7, 8, and 9) extending between a second ring (5) and a first ring (6).

Figure 12:
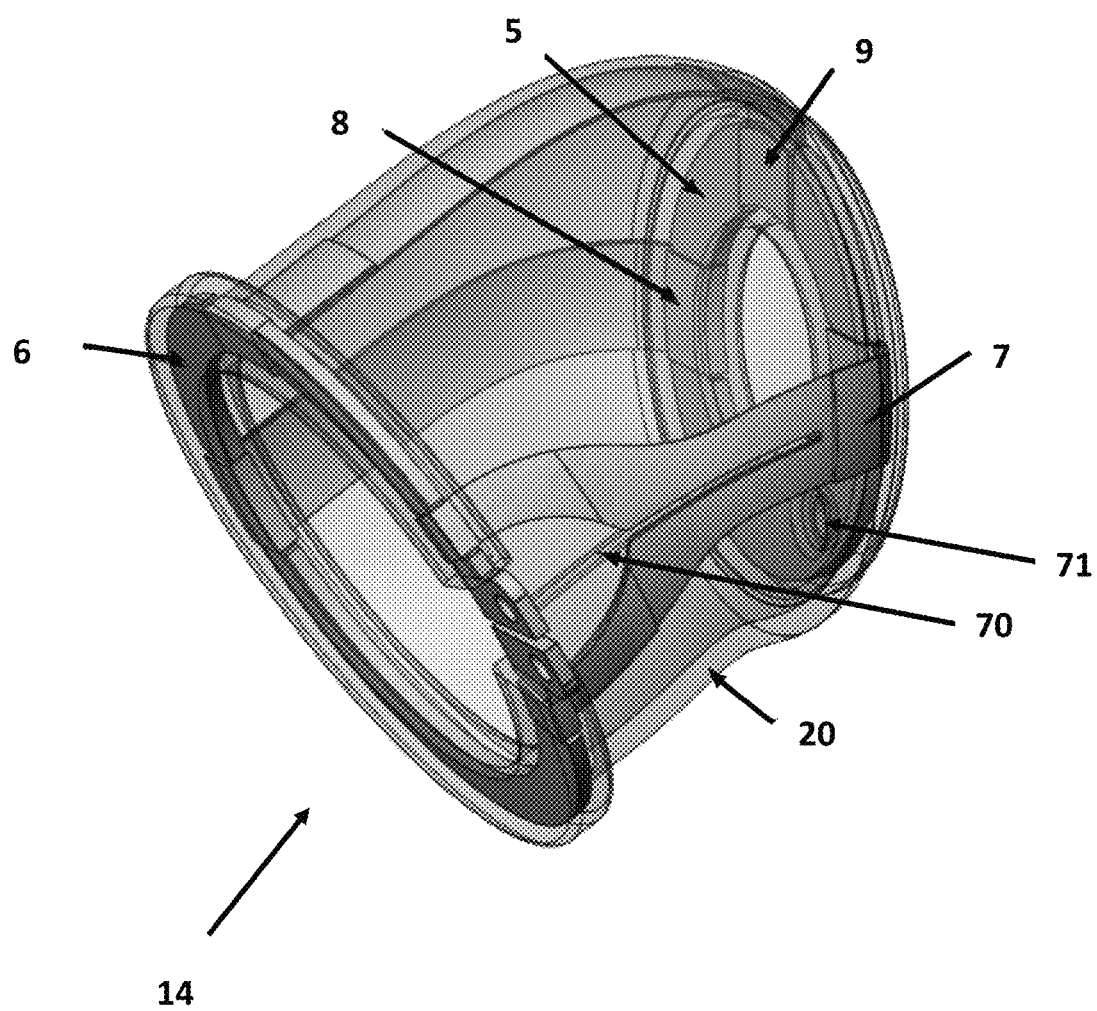
FIG. 12 shows an exemplary retainer assembly (14) for shoulder arthroplasty.

FIG. 12 shows an exemplary retainer assembly (14) for shoulder arthroplasty. This assembly is composed of an exemplary band assembly (13), and includes a retainer assembly outer sleeve (20) that surrounds the band assembly. The retainer outer sleeve contains a split region (70) that allows the sleeve to be opened up to a larger size to fit over the humeral assembly and capture it at its first ring recess (35). The retainer outer sleeve also includes an opening (71) that corresponding with the hole in the second ring (5).

Figure 13A:
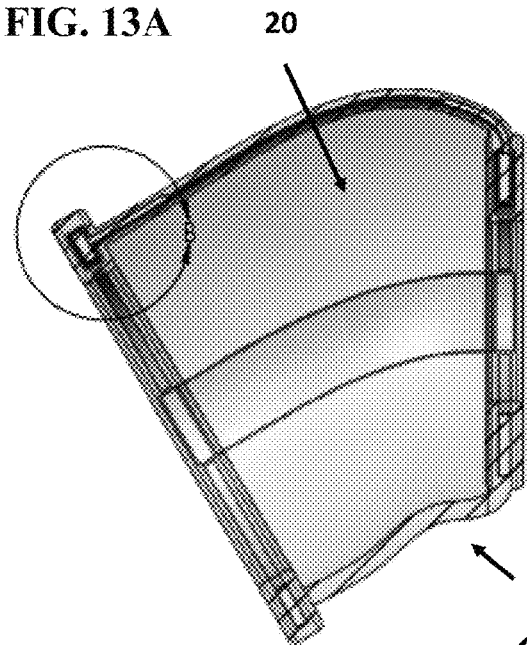
Figure 13B:
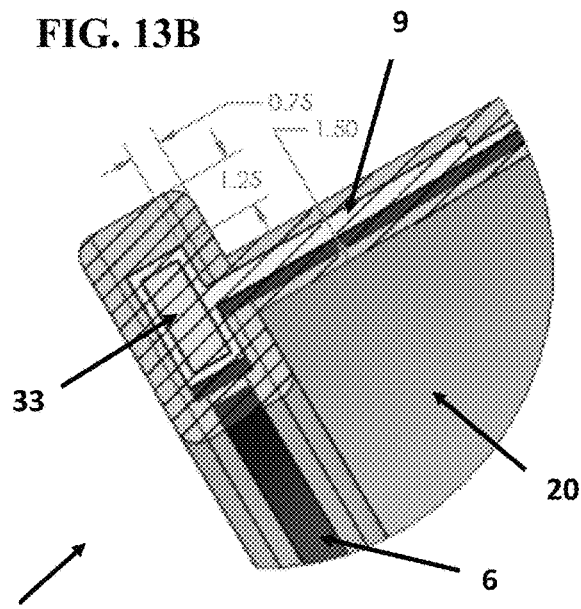
Figure 13C:
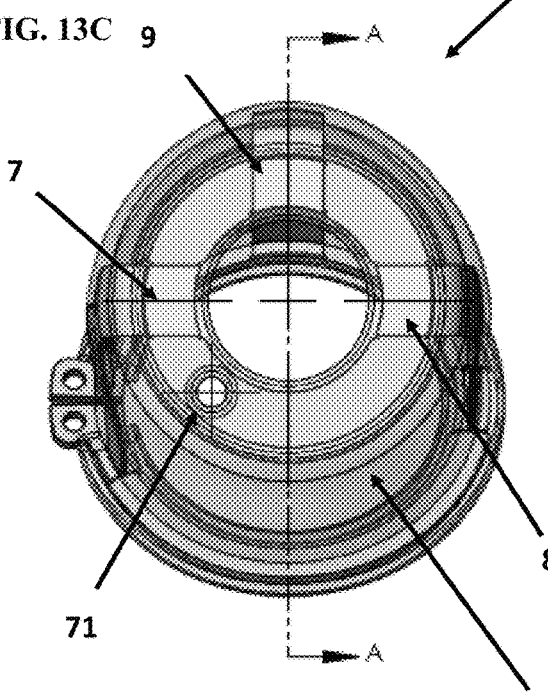

FIGS. 13A-D shows various views of an exemplary retainer assembly (14) employing three flexible straps. FIG. 13A shows a side view of an exemplary retainer assembly (14). FIG. 13B shows detail "B" from FIG. 13A, showing the first ring end (33) of the flexible band (9). FIG. 13C shows a bottom view of the exemplary retainer assembly (14), including a hole (71) in the retainer assembly outer sleeve (20). FIG. 13D shows a cross section through A-A of FIG. 13C.

Figure 14:
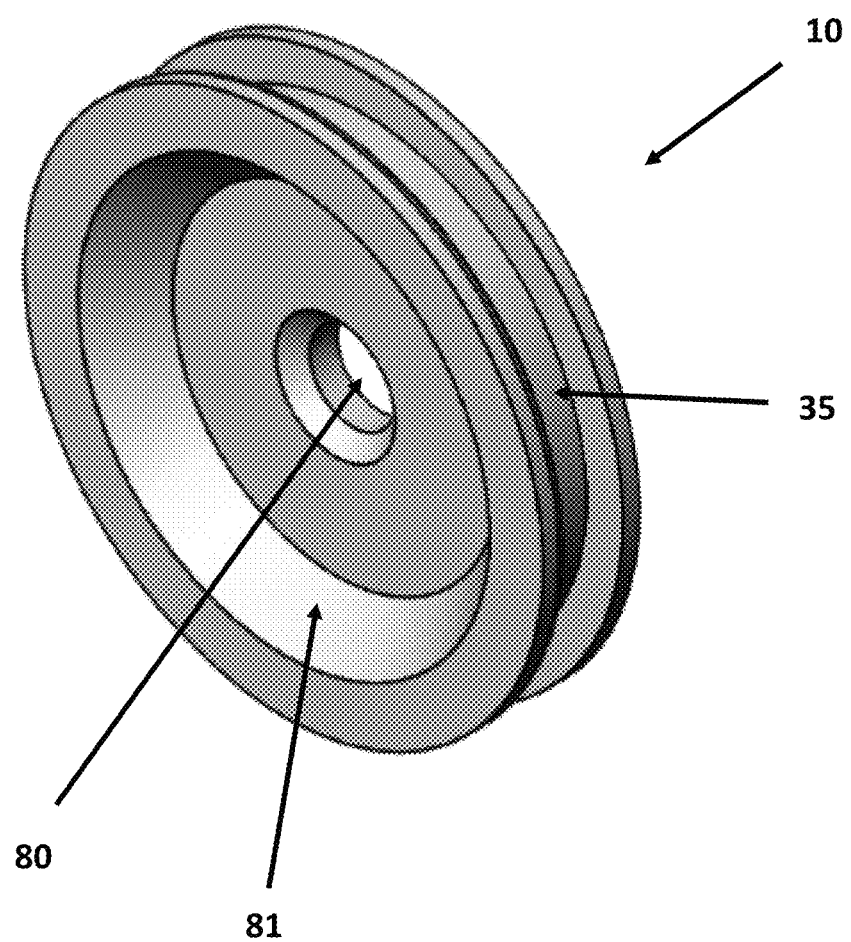
FIG. 14 shows an exemplary humeral adapter tray (10).

FIG. 14 shows and exemplary humeral adapter tray (10), which contains a recess (81) to accept a humeral liner (11). The adapter tray (10) has a peripheral recess (35) to accept the first ring (e.g., nitinol snap ring), and a central hole (80) to accept screw (12). This screw links the adapter tray (10) and humeral liner (11) to a threaded hole in a humeral stem.

Figure 15:
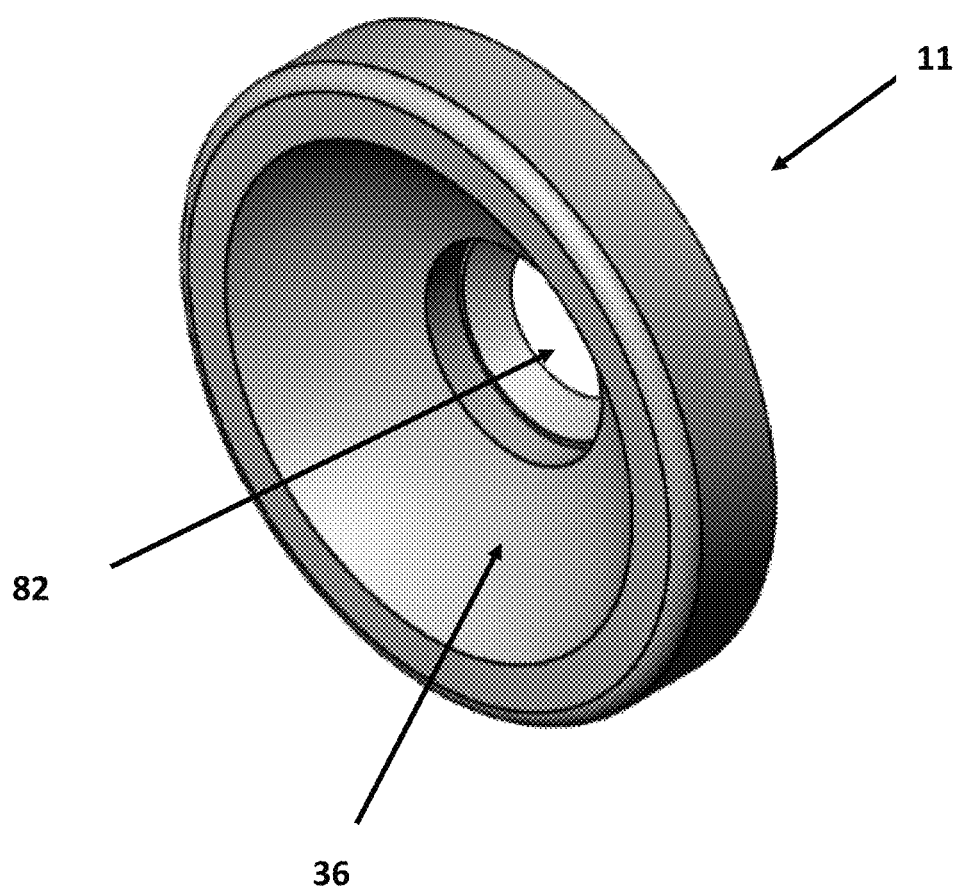
FIG. 15 shows an exemplary humeral liner (11).

FIG. 15 shows an exemplary humeral liner (11), which may be composed of UHMWPE, or similar material. It contains a 40 degree bevel on the bottom to mate with the humeral adapter tray (10), a glenosphere recess (36) on the top which articulates with the glenosphere (4), and a central hole (82) to accept a screw (12). The radius of curvature of the glenosphere recess (36) generally matches that of the glenosphere (4), thereby allowing conforming articulation.

It is noted that the humeral adapter tray (10) and humeral liner (11) could be a single unitary component, making up the humeral baseplate (34). In particular embodiments, it is more advantageous to have separate components 10 and 11 to allow height adjustment in vivo to match patient anatomy.

In other embodiments, (e.g., as in hip arthroplasty), a single unitary component may be employed.

FIG. 16A shows the assembly of the exemplary humeral adapter tray (10) and exemplary humeral liner (11) onto a humeral stem using a screw (12). FIG. 16B shows the components assembled on the humerus bone.

Figure 17:
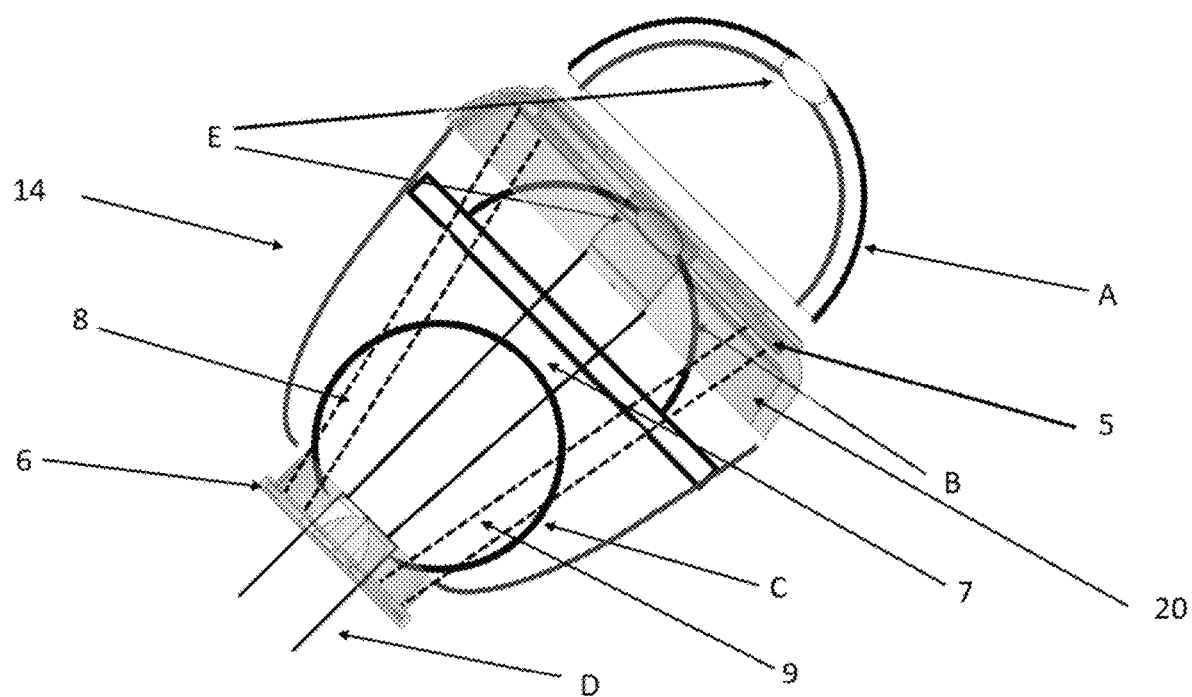
FIG. 17 shows an exemplary retainer assembly (14) for hip joint arthroplasty.

FIG. 17 shows an exemplary retainer assembly (14) for hip joint arthroplasty. FIG. 17 depicts how the fully constrained retainer assembly could be employed for total hip replacement. "A" is the acetabular component, "B" is the acetabular liner, "C" is the femoral head, "D" is the trunnion of the femoral stem, and "E" is a hole in A (threaded) and B (non-threaded) which could accept a fastening screw (not shown), thereby capturing the second ring (5) and preventing dissociation of parts A and B in vivo. The hip retainer assembly (14) is composed of the second ring (5) and first ring (6) with bands 7, 8, and 9 stretching therebetween. The retainer assembly outer sleeve (20) is partially shown and can be a liquid silicone rubber over-mold, which is pliable.

Figure 18A:
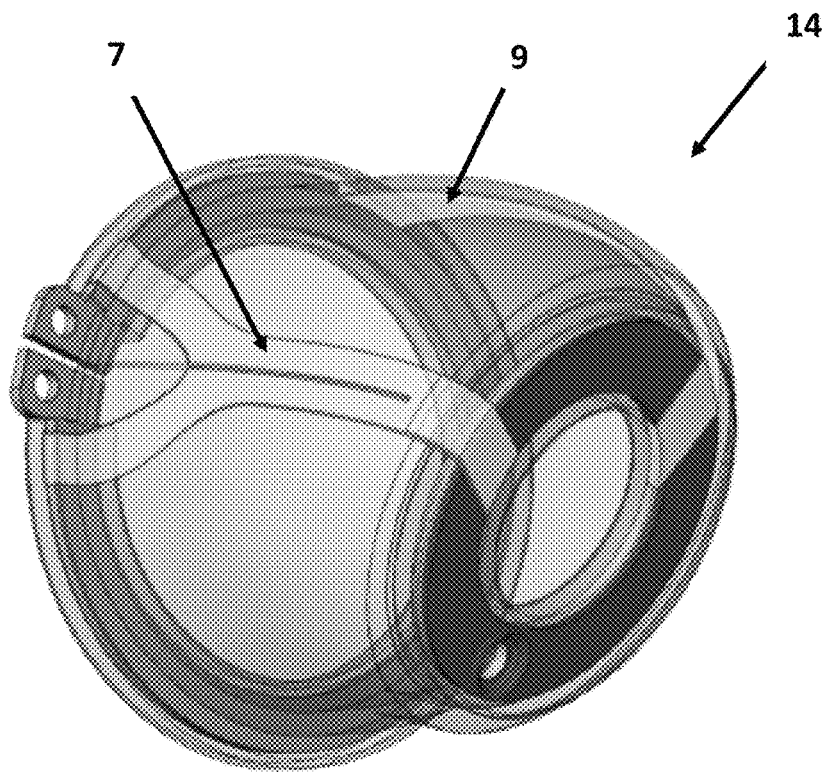
FIGS. 18A and 18B show a retainer assembly.
Figure 18B:
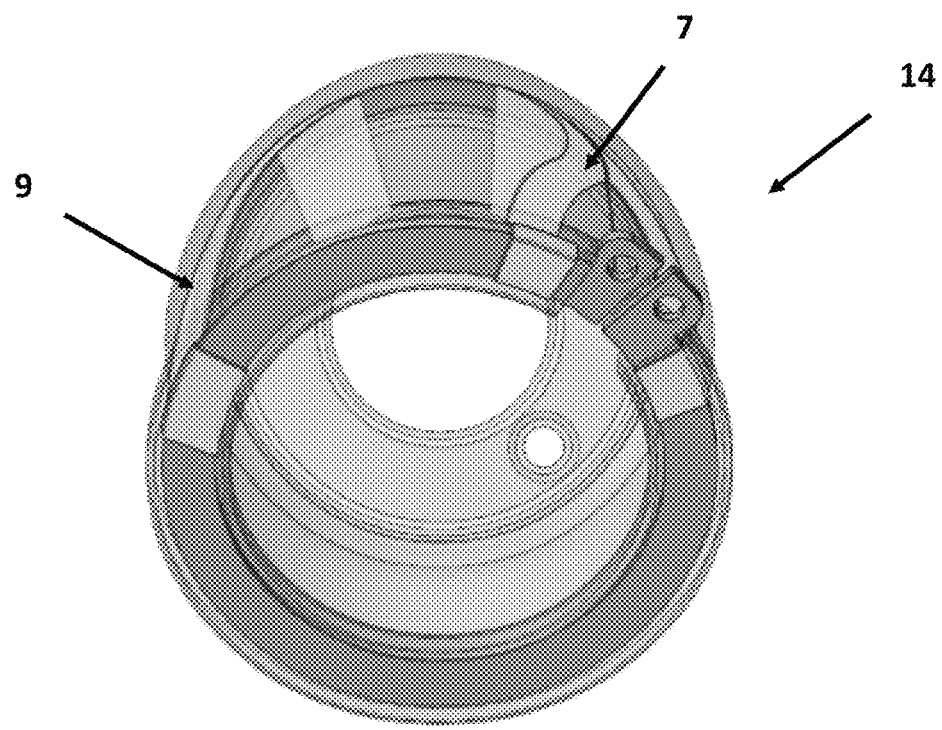

FIG. 18A shows a first view of a retainer assembly (14) employing two flexible bands (7 and 9). FIG. 18B is a second view of a retainer assembly (14) employing two flexible bands (7 and 9).

The exemplary steps for implanting the components of the systems herein (using exemplary components) into a subject's shoulder are as follows. The shoulder is exposed via a standard deltopectoral approach. A guidewire is placed in the correct position on the glenoid, ensuring neutral version and inferior tilt. Reaming is performed until the appearance of bleeding subchondral bone. The scapular baseplate (part 1) is inserted over the guidewire. Two peripheral non-locking screws (part 3) are then placed through the superior and inferior holes in the baseplate. The guidewire is withdrawn. A central locking compression screw (part 2) is then inserted. The retainer assembly (part 14) is then placed onto the baseplate such that the second ring (part 5) is aligned with the baseplate dowel pin. The glenosphere (part 4) is then secured onto the central threaded post of the baseplate with an appropriate driver.

Attention is then turned to the humerus. The canal is prepared with reamer and broach. The humeral stem is inserted with either press-fit or cemented technique per surgeon discretion. The humeral adapter tray and liner (parts 10 and 11) are then placed onto the humeral stem and secured with a fastening screw (part 12). Snap ring pliers are applied to the first ring (part 6) of the retainer assembly to open the ring. The humeral assembly is delivered en bloc into the retainer assembly and the shoulder joint is reduced (e.g., glenosphere mated to the glenosphere recess). The snap ring pliers are withdrawn and the nitinol ring closes around the humeral adapter tray, securing itself within the peripheral recess. The surgeon then places running or interrupted sutures around the anterior Y-shaped band and into the retainer assembly to close down the anterior split. The nitinol ring is closed with suture passed through the snap ring holes at the surgeon's discretion.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. An apparatus comprising:
   a) a scapular baseplate comprising:
      i) a scapular bone connecting component,
      ii) a dowel pin, and
      iii) a glenosphere base connecting component;
   b) a humeral baseplate comprising:
      i) a humeral bone, and/or humeral stem, connecting component,
      ii) a glenosphere recess, and
      iii) a first ring connecting component which comprises a circular peripheral recess that accepts a first retaining ring,
   c) a glenosphere comprising:
      i) a top surface that articulates with said glenosphere recess, and
      ii) a bottom surface that attaches to said glenosphere base connecting component of said scapular baseplate;
   d) a retainer assembly comprising:
      i) said first retaining ring which is expandable by force at a first and second hole, wherein said first retaining ring comprises: A) said first hole adjacent to said second hole, B) first and second flexible band attachment or holder sites, on opposite sides of said first and second holes, which accept two ends of a first flexible band that is Y-shaped, C) a third flexible band attachment or holder site which accepts a second flexible band; and D) a fourth flexible band attachment or holder site which accepts a third flexible band,
      ii) a second ring, wherein said second ring comprises: A) a first flexible band attachment or holder site which accepts said first flexible band, B) a second flexible band attachment or holder site which accepts said second flexible band; C) a third flexible band attachment or holder site accepts said third flexible band, and D) a scapular baseplate connecting component which comprises a hole that accepts said dowel pin of said secular baseplate,
      iii) said first flexible band that is Y-shaped: A) attached to, or configured to be attached to or held by, said second ring at said first flexible band attachment or holder site, and B) attached to, or configured to be attached to or held by, said first retaining ring at both said first and second flexible band attachment or holder sites,
      iv) said second flexible band: A) attached to, or configured to be attached to or held by, said second ring, and B) attached to, or configured to be attached to or held by, said first retaining ring, and
      v) said third flexible band: A) attached to, or configured to be attached to or held by, said second ring, and B) attached to, or configured to be attached to or held by, said first ring.

2. The apparatus of claim 1, wherein said first, second, and third flexible band attachment or holder sites are notches or protrusions in said first retaining ring and in said second ring.

3. The apparatus of claim 1, wherein said first flexible band would be in an anterior position when said apparatus is assembled in a subject's shoulder area, wherein said second flexible band would be in a posterior position when installed in said subject's shoulder area, and wherein said third flexible band would be in a superior position when installed in said subject's shoulder area.

4. The apparatus of claim 1, wherein said retainer assembly further comprises a retainer assembly outer sleeve that extends from said first retaining ring to said second ring covering one or both sides of said first and second flexible bands.

5. The apparatus of claim 4, wherein said retainer assembly outer sleeve surrounds said glenosphere and glenosphere recess when installed in a subject's shoulder area.

6. The apparatus of claim 4, wherein said retainer assembly outer sleeve comprises a biocompatible flexible material.

7. The apparatus of claim 6, wherein said biocompatible flexible material comprises silicone.

8. The apparatus of claim 4, wherein said retainer assembly outer sleeve comprises: i) a generally cylindrical outer wall, ii) a lateral split in said cylindrical wall, and iii) an aperture for said dowel pin of said scapular bone connecting component.

9. The apparatus of claim 1, wherein said scapular baseplate comprises titanium.

10. The apparatus of claim 1, wherein said scapular bone connecting component comprises two or three apertures each sized for a bone screw.

11. The apparatus of claim 10, further comprising two or three of said bone screws.

12. The apparatus of claim 1, wherein said scapular baseplate has a diameter between 25 and 31 mm.

13. The apparatus of claim 1, wherein said dowel pin, when inserted into a dowel pin aperture, prevents said second ring from rotating when said apparatus is assembled in a subject's shoulder area.

* * * * *